(12) United States Patent
Muramatsu

(10) Patent No.: US 7,395,542 B2
(45) Date of Patent: Jul. 1, 2008

(54) DISK APPARATUS

(75) Inventor: Akira Muramatsu, Osaka (JP)

(73) Assignee: Funai Electric Co., Ltd., Osaka (JP)

(*) Notice: Subject to any disclaimer, the term of this patent is extended or adjusted under 35 U.S.C. 154(b) by 394 days.

(21) Appl. No.: 11/311,336

(22) Filed: Dec. 20, 2005

(65) Prior Publication Data
US 2006/0136942 A1    Jun. 22, 2006

(30) Foreign Application Priority Data
Dec. 21, 2004   (JP)   .......................... P2004-369968

(51) Int. Cl.
*G11B 17/04* (2006.01)
(52) U.S. Cl. ........................................ 720/605
(58) Field of Classification Search ................. 720/600, 720/605, 612; 369/30.78
See application file for complete search history.

(56) References Cited

FOREIGN PATENT DOCUMENTS

| JP | 5-198068 | 8/1993 |
|---|---|---|
| JP | 5-266564 | 10/1993 |
| JP | A-06-251479 | 9/1994 |
| JP | 2001-222847 | 8/2001 |

*Primary Examiner*—Joseph Feild
*Assistant Examiner*—Mark Blouin
(74) *Attorney, Agent, or Firm*—Morgan, Lewis & Bockius LLP

(57) ABSTRACT

A disk apparatus, in which, when a tray is forcibly pushed into a case in the rearward direction with a driving chassis stopped in a downwardly moved state by turning off a power source, the tray returns to the interior of the case. In the disk apparatus, projections of a synthetic resin are extended downward from the portions of a lower surface of the top plate of the case which are close to a rear portion of the tray stored in the case. The lower ends of the projections are positioned lower than an upper surface of the tray.

3 Claims, 7 Drawing Sheets

DISK APPARATUS

BACKGROUND OF THE INVENTION

1. Field of the Invention

The present invention relates to a disk apparatus for carrying out a reproduction, recording and erasing of information registered in a disk, for example, a DVD player, and more particularly to a disk apparatus for moving a tray forward and backward smoothly by preventing a so-called avalanche phenomenon of a disk and without damaging the disk.

2. Description of the Related Art

The examples of the related art DVD players include an example shown in FIGS. 6, 7A, and 7B. In this example, a rectangular box type case 1 is formed by a top plate 1a, a bottom plate 1b and a front plate 1c, and provided at one front side corner portion with an apparatus body 2. Around the apparatus body 2 in the case 1, a substantially L-shaped AV printed board 3 in plan and a rectangular main printed board 4 are provided.

The apparatus body 2 has a main chassis 8 supporting a tray 17 adapted to place a disk D thereon so that the tray can be moved forward a and backward b, and a drive chassis 13 which is supported on the main chassis 8 so that the drive chassis can be moved up c and down d around a pivot 9, and which is mounted with a spindle motor 12 provided with an optical pickup 10 and a turntable 11. A cam shaft 14 projecting from a front surface of the drive chassis 13 is fitted in a cam hole 15a of a cam slider 15, and the cam slider 15 is provided on the main chassis 8 so that the cam slider can be slid in the lateral directions e, f which orthogonally cross the longitudinal directions a, b. When the cam slider 15 is slid in the leftward direction e (or rightward direction f), the drive chassis 13 is moved in the vertical directions c, d. A magnet-carrying disk holder 17 opposed to the turntable 11 is set on lateral beam 18 provided between both side walls 8a of the main chassis 8 so that the disk holder can be moved up and down within a predetermined range. Referring to FIG. 1, a reference numeral 19 denotes a disk storage recess formed in a central portion of the tray 7, and 20 a floatation preventing members extending from both side walls 8a of the main chassis 8 to positions above both side edge recesses 7a of the tray 7.

The principle of the actions of this structure will be described. The solid lines in FIG. 6, and FIG. 7A show a playing mode. The disc D is rotated at a high speed by the spindle motor 12 via the turntable 11, and the information recorded in the disk D is read by the optical pickup 10, an image being reproduced on the monitor.

When an unloading signal is inputted from the playing mode, the cam slider 15 is slid leftward e (or rightward f) as shown in FIG. 7B to cause the driving chassis 13 to be moved down d. As a result, after the disk D is transferred from the turntable 11 to the tray 7, the tray 7 is advanced forward a through a disk takeout port 21 of the front plate 1c. The disk D is then taken out from the tray 7, and a new disk D is placed on the tray 7.

When a loading signal is then inputted, the tray is moved back b as shown in FIG. 7A to cause the tray 7 to be moved back b and stored in the interior of the case 1. The cam slider 15 is then slid rightward f (or leftward e) to move the driving chassis upward c and hold the disk D on the tray between the turntable 11 and disk holder 17.

According to the structure, when the power source is turned off on the basis of the unloading signal as shown by solid lines in FIG. 8 with the tray 7 in an forwardly a advanced state, the drive chassis 13 is stopped in a downwardly d moved state. When the tray 7 is forcibly pushed by fingers in the backward b direction and thereby return the tray 7 into the interior of the case 1, the disk D on the tray 7 is held between the turntable 11 and disk holder 17 with the turntable 11 in a lowered state as shown by solid lines in FIG. 8.

When the case is inclined as shown in phantom as shown in FIG. 8, so as to, for example, transport the case 1 to another place with the disk D not held as in the above-described state, the disk D stored in the disk storage recess 19 is disengaged therefrom in the backward b direction. As a result, the disk D is disengaged from a proper position to the extent that a rear half portion of the disk D projects from the tray 7 as shown in a position shown by . . . , and a so-called avalanche phenomenon occurs.

When the power source is turned on in this condition to cause the tray 7 to be moved forward a on the basis of an unloading signal, there is the possibility that the disk D is left in a rear position and falls into the case 1, and that the disk D is held between the forwardly a moving tray 7 and lateral beam 18.

As examples of the related techniques solving these problems, there are techniques disclosed in JP-A-6-251479. In the techniques, a hook is projected from a circumferential edge of a disk storage recess 19 of a tray 7 so as to thereby prevent by inclining a case 1 a disc D from being disengaged from the disk storage recess 19.

SUMMARY OF THE INVENTION

In the above-described related art structure, the height h of the hook 22 is set small [refer to FIG. 10A] so that the hook 22 does not contact the lateral beam 18 when the tray 7 is moved forward and backward a, b. Therefore, the disk D gets over the hook 22 and is disengaged therefrom in the backward b direction in some cases [Refer to the two-dot solid line in FIG. 10A] due to a shock occurring when the case 1 is inclined. In the meantime, a distance α between the hook 22 and lateral beam 18 is set small by projecting the hook 22, so that, when the tray 7 is moved forward a on the basis of an unloading signal, the disk D is held between the hook 22 and lateral beam 18 as shown in FIG. 10B. Therefore, there is the possibility that the disk D is damaged, and that the forward a movement of the tray 7 is prevented.

The present invention has been made in view of the above circumstances and provides a disk apparatus adapted to move a tray forward and backward smoothly by eliminating a so-called avalanche phenomenon of the disk without damaging the disk.

According to an aspect of the invention, a disk apparatus in which a rectangular box type case is formed by a top plate, a bottom plate and a front plate, an apparatus body provided in the case having: a main chassis supporting a tray, on which a disk is placed, in such a manner that the tray can be moved forward and backward; and a driving chassis which is supported pivotably on the main chassis so that the driving chassis can be moved up and down, and which is mounted with an optical pickup and a turntable, a hook being projected from a circumferential portion of a disk storage recess of the tray, the disk being rotated at a high speed by the turntable, from a playing mode, in which the information recorded in the disk is read by the optical pickup, the driving chassis being moved up and down on the basis of an unloading signal, the disk being thereby handed over from the turntable to the tray, the tray being thereafter moved forward through a disk takeout port of the front plate, the disk being taken out from the tray with a new disk placed on the tray, a power source being turned off to stop the driving chassis in a downwardly moved state with the tray forcibly pushed in the rearward direction so that the tray is returned to the interior of the case the disengagement of the disk from the interior of the disk storage recess of the tray being prevented by the hook by inclining the case, characterized in that; the hook is removed, projections being extended downward from the portion of a lower surface of the top plate which is close to a rear portion of the tray stored in the case, the projections being positioned at lower ends thereof lower than an upper surface of the tray, the case being made of a synthetic resin, the top plate of the case and projections being formed so as to be integral with each other.

According to another aspect of the invention, a disk apparatus having a rectangular box type case formed by a top plate, a bottom plate and a front plate, an apparatus body provided in the case, the apparatus body having a main chassis supporting a tray, on which a disk is placed, in such a manner that the tray can be moved forward and backward, and a driving chassis which is supported pivotably on the main chassis so that the driving chassis can be moved up and down, and which is mounted with an optical pickup, the disk being rotated at a high speed by a turntable, from a playing mode in which the information recorded in the disk is read by the optical pickup, the driving chassis being moved up and down on the basis of an unloading signal, the disk being thereby handed over from the turntable to the tray, the tray being thereafter moved forward through a disk takeout port of the front plate, the disk being taken out from the tray with a new disk placed on the tray, a power source being turned off to stop the driving chassis in a downwardly moved state with the tray forcibly pushed in the rearward direction so that the tray is returned to the interior of the case, characterized in that projections of a synthetic resin are extended downward from the portions of a lower surface of the top plate which are close to a rear portion of the tray stored in the case, lower ends of the projections being positioned lower than an upper surface of the tray.

According to another aspect of the invention, the case is made of a synthetic resin. The top plate and projections of the case being molded are integrally formed one another.

BRIEF DESCRIPTION OF THE DRAWINGS

These and other objects and advantages of this invention will become more fully apparent from the following detailed description taken with the accompanying drawings in which.

DESCRIPTION OF THE PREFERRED EMBODIMENTS

Figure 1:
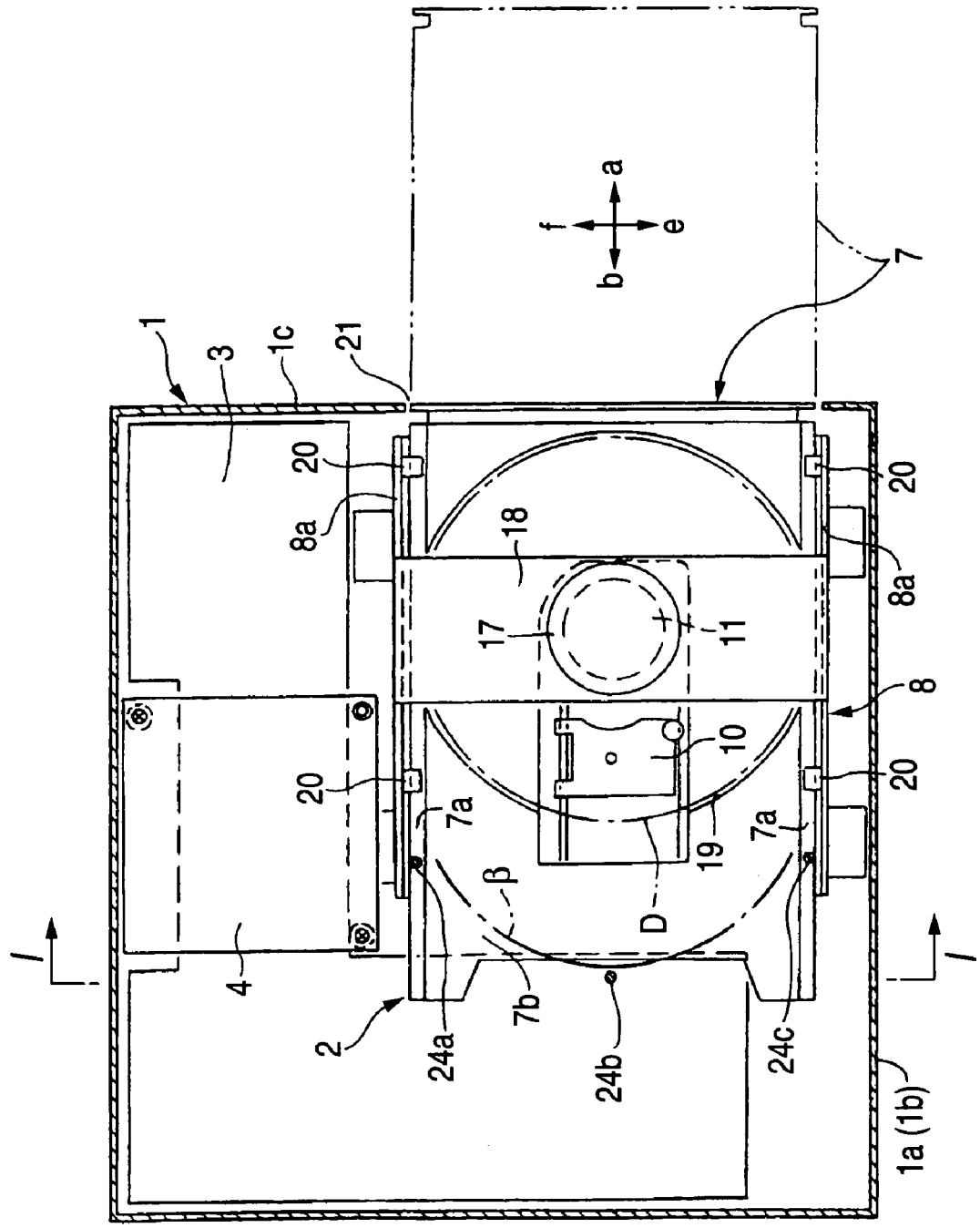
FIG. 1 is a horizontal sectional view of a disk apparatus according to an embodiment of the present invention.
Figure 2:
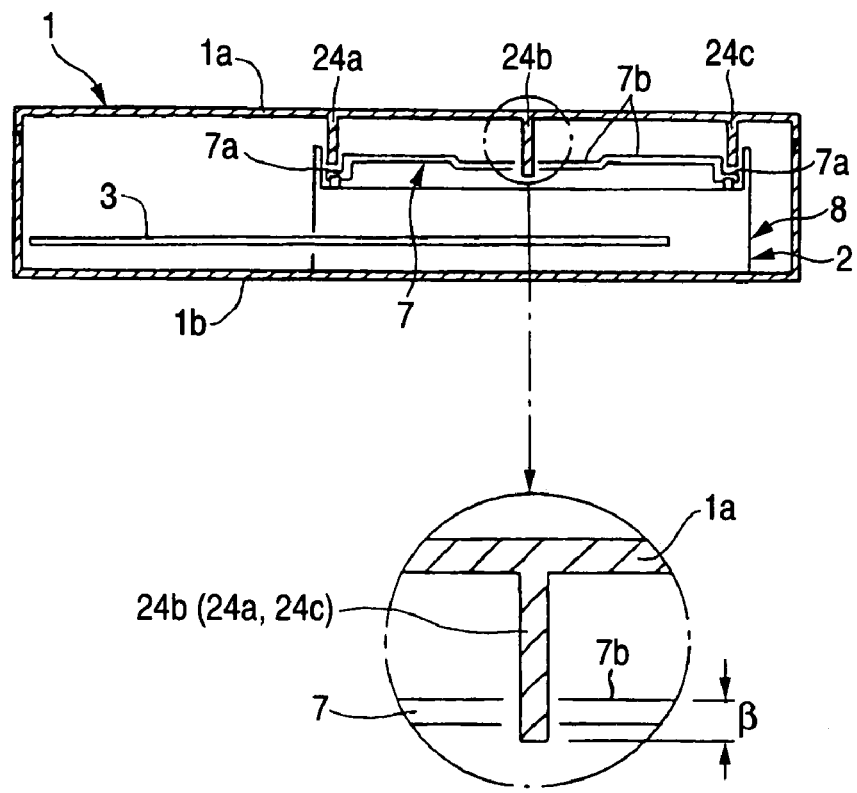
FIG. 2 is a drawing taken in the direction of arrows I-I in FIG. 1.
Figure 3:
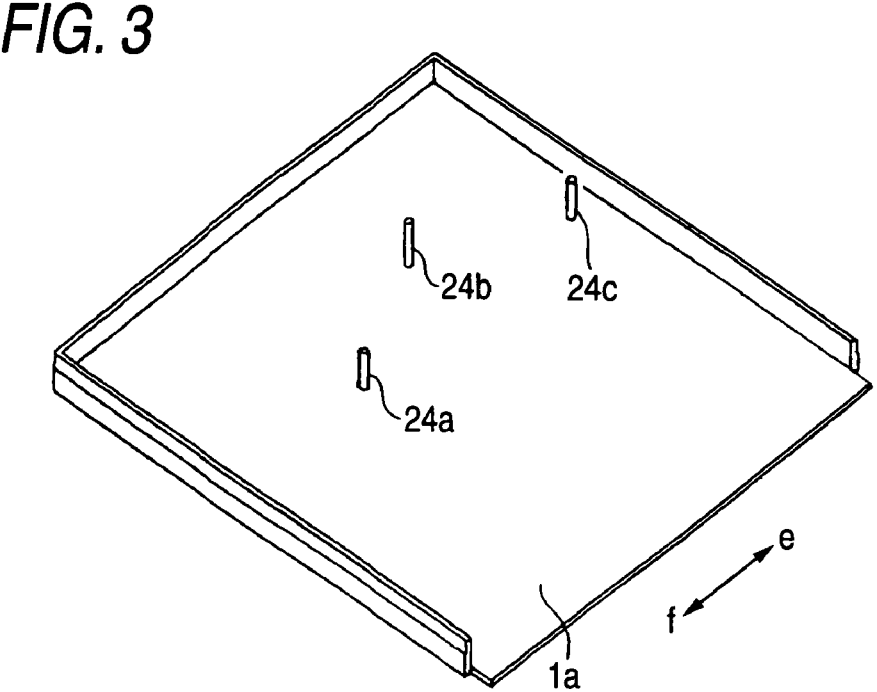
FIG. 3 is a perspective view of a principal portion of the embodiment.

FIG. 1 to FIG. 3 show a DVD player (disc apparatus) according to an embodiment of the invention, in which projections 24a to 24c are provided so as to extend downward from the portions of a lower surface of a top plate 1a which are close to a rear portion of a tray 7 stored in a case 1. The construction of the parts other than that of the remaining parts is substantially identical with that of the corresponding parts shown in FIG. 6 and FIGS. 7A, 7B. Therefore, the same reference numerals are added to the same parts, and a description thereof is omitted.

The case 1 is molded out of a synthetic resin, and the top plate 1a and projections 24a to 24c are molded so as to be integral with one another. This enables the top plate 1a having projections 24a to 24c to be mass-produced inexpensively.

In the embodiment, three projections 24a to 24c are provided at predetermined intervals in the lateral directions e, f along an outer circumference . . . (refer to FIG. 1) of the disk D, which is disengaged from the disk storage recess 19 in the backward direction b, and the central projection 24b is positioned in the central portion, which is immediately behind the central portion, of a rear edge of the tray 7. The left and right projections 24a, 24c are positioned so that the free ends thereof are above the surfaces of recesses 7a at both side edges of the tray 7, and lower ends of the projections 24a to 24c are positioned below an upper surface 7b of the tray by a predetermined distance β.

Figure 4:
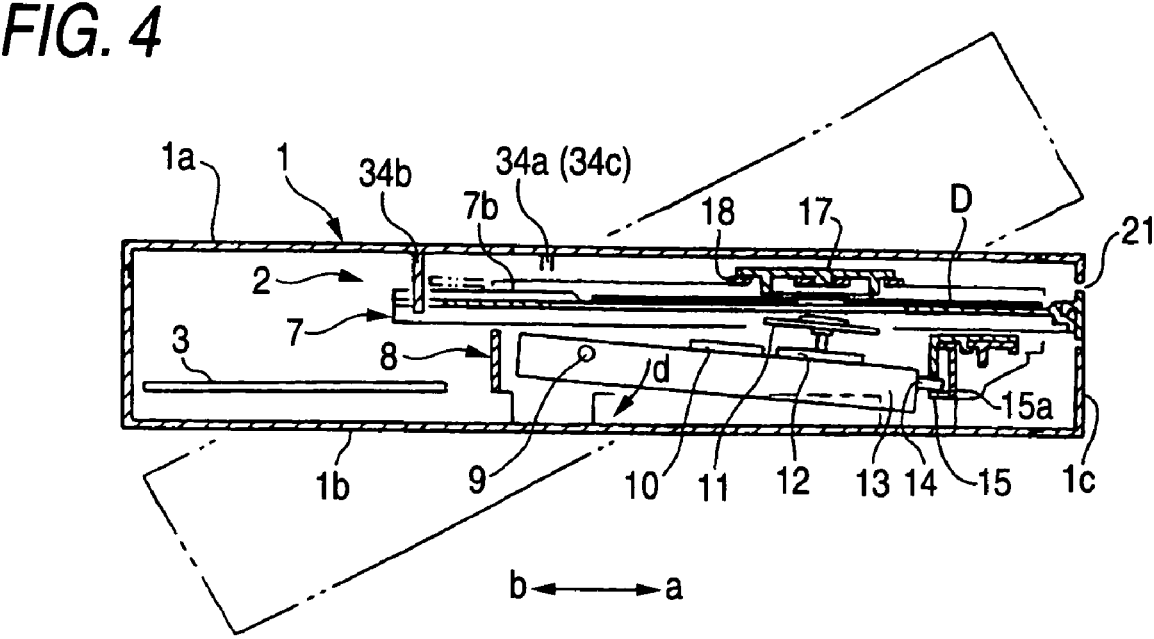
FIG. 4 is a longitudinal sectional view showing a disk disengagement-prevented state.
Figure 5A:
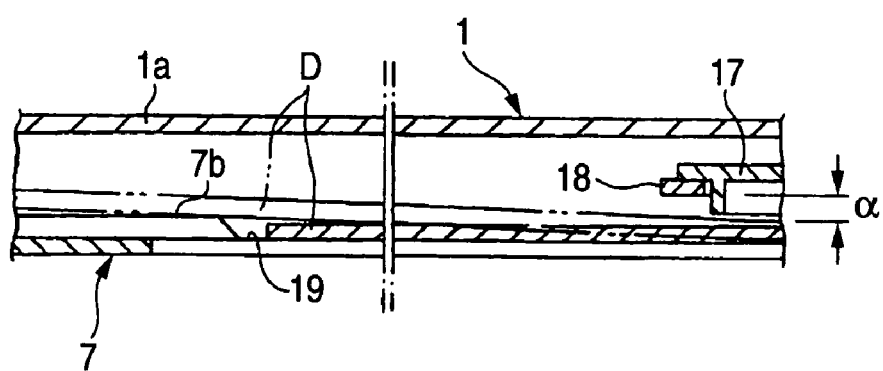
FIG. 5A is an enlarged longitudinal sectional view of a principal portion of the same principal portion in a first half of the disk disengagement-preventing operation.
Figure 5B:
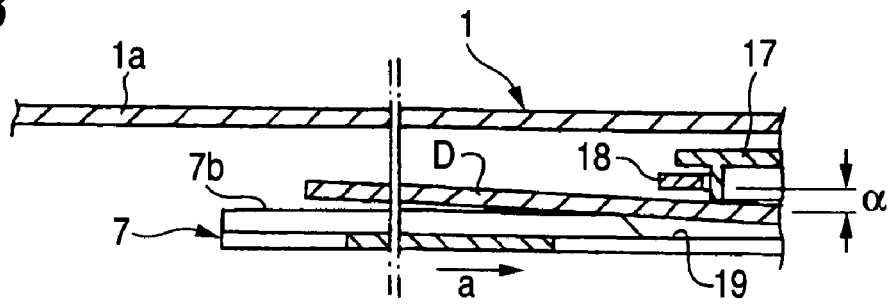
FIG. 5B is an enlarged longitudinal sectional view of the same principal portion in a latter half of the disk disengagement-preventing operation.
Figure 6:
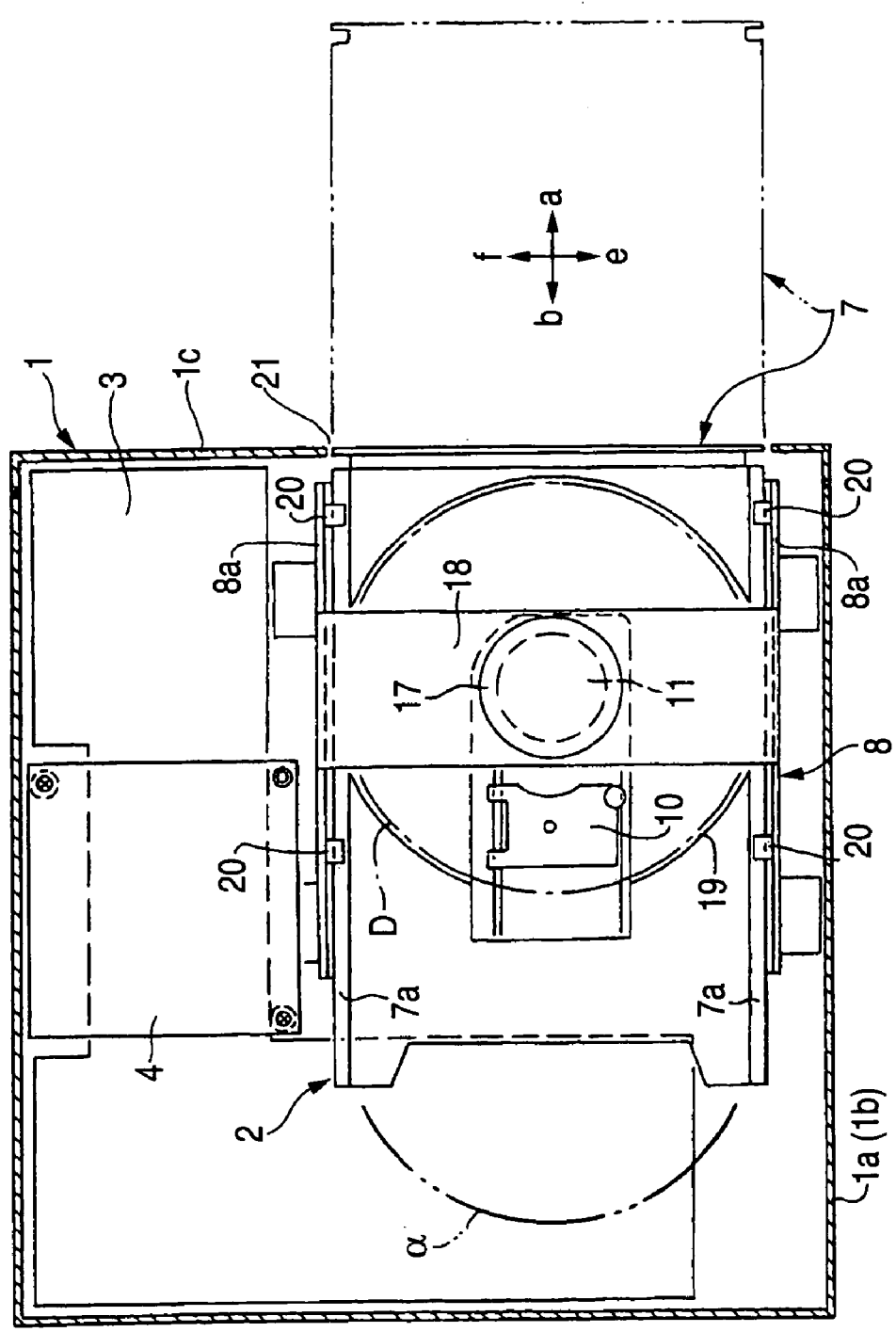
FIG. 6 is a horizontal sectional view according to a related art.
Figure 7A:
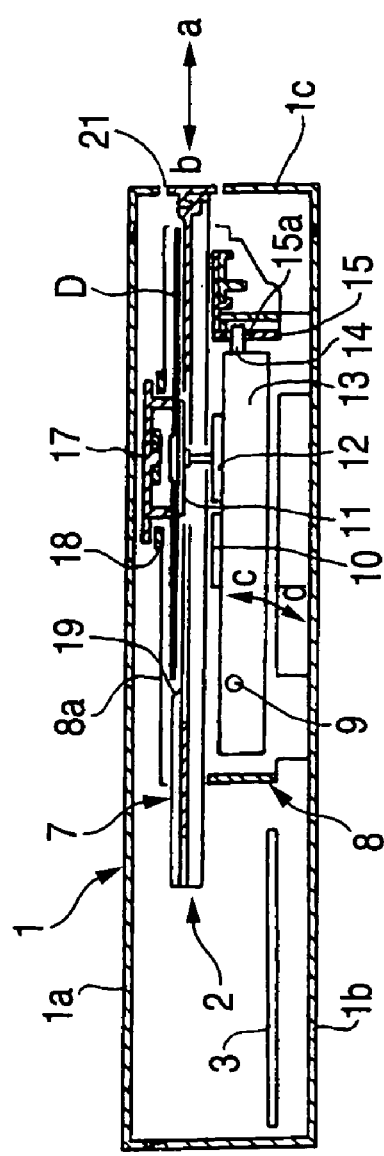
FIG. 7A is a longitudinal sectional view showing a playing mode.
Figure 7B:
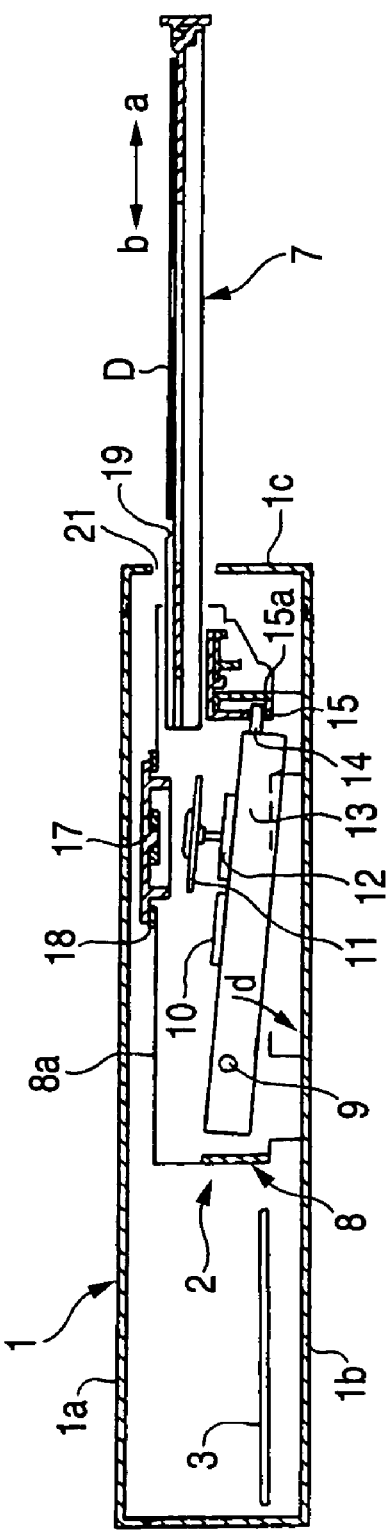
FIG. 7B is a longitudinal sectional view showing an unloading state.
Figure 8:
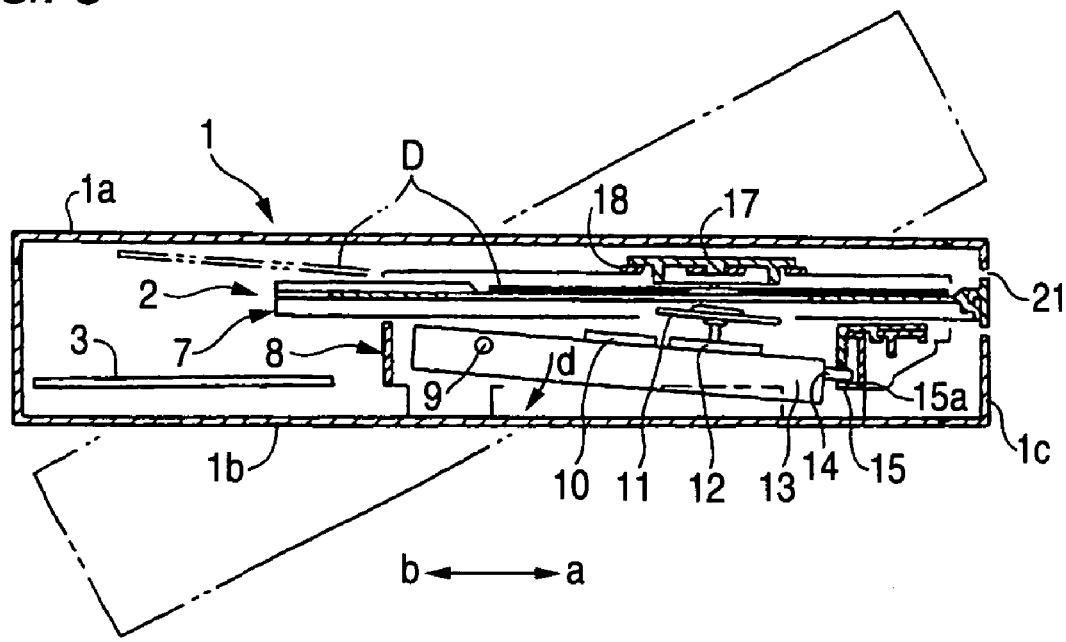
FIG. 8 is a longitudinal sectional view showing a recess-disengaged state according to the related art.
Figure 9:
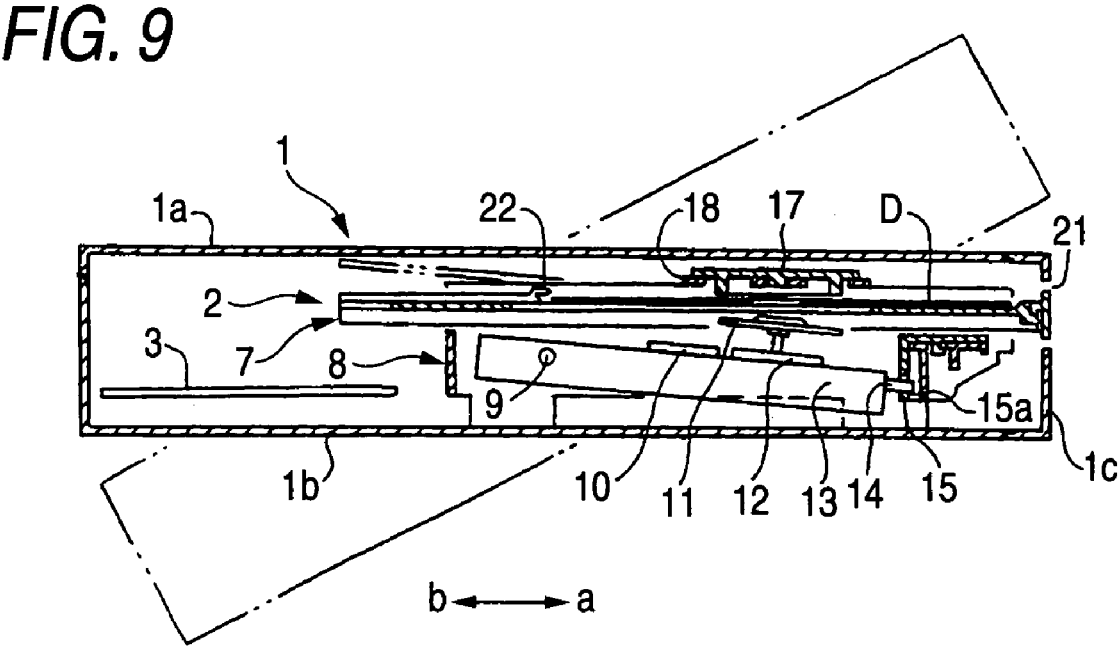
FIG. 9 is a longitudinal sectional view according to another related art.
Figure 10A:
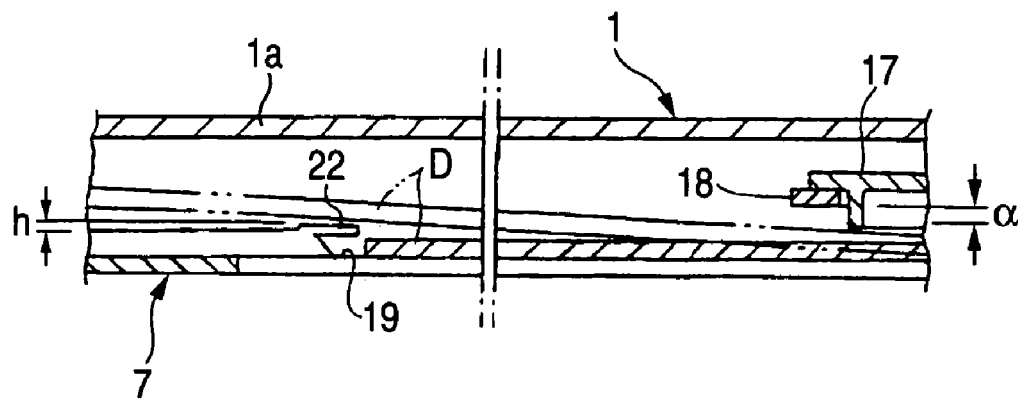
FIG. 10A is an enlarged longitudinal sectional view of a principal portion of this example, showing a first half of a recess-disengagement preventing operation.
Figure 10B:
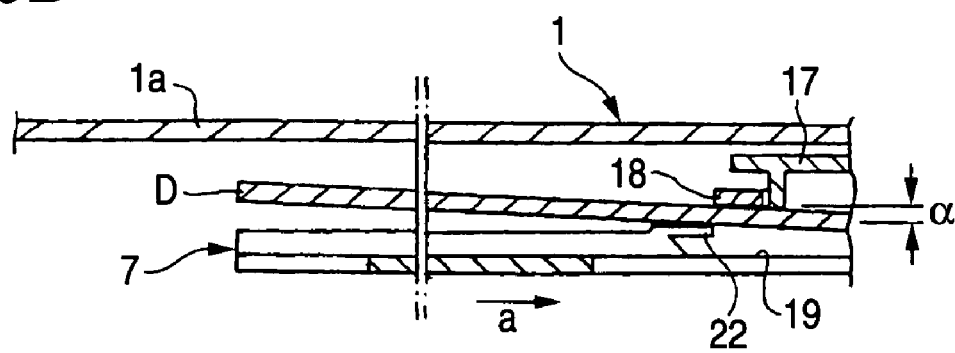
FIG. 10B an enlarged longitudinal sectional view of a principal portion of the example, showing a latter half of the recess-disengagement preventing operation.

Since the principles of of the embodiment is substantially identical with those of the actions of the related art example shown in FIG. 6 and FIGS. 7A, 7B, a description thereof is omitted. As shown in FIG. 4, the drive chassis 13 is stopped in a downwardly moved state d by turning off the power source, and the tray 7 is forcibly pushed backward b into the case by fingers. When the disk D on the tray is thereby not held between the turntable 11 and disk holder 17, the case 1 is inclined so as to, for example, transport the case to some other place. As a result, the disk D stored in the disk storage recess 19 is disengaged therefrom in the backward direction as shown in FIG. 5A. Since the projections 24a to 24c are provided vertically on the portion of the lower surface of the top plate 1a which is close to the rear portion of the tray 7, the disk D does not get over the projections 24a to 24c, and is not disengaged from the disk storage recess in the backward direction b. Since the lower ends of the projections 24a to 24c are positioned lower than the upper surface 7b of the tray, the disc D is not disengaged from the recess in the backward direction through a space under the projections 24a to 24c. Therefore, the occurrence of a so-called avalanche phenomenon can be prevented reliably, and the disk can be stayed on the tray 7. When the tray 7 is moved forward a on the basis of the unloading signal as shown in FIG. 5B, the disk D can be taken out smoothly to the outside of the case 1 owing to the forward a movement of the tray since a distance α, which is sufficiently larger than the thickness of the disk, between the upper surface 7b of the tray and the lateral beam 18 is secured.

Since the projections 24a to 24c are made of a synthetic resin, there is not the possibility that electric short-circuiting occurs between the projections 24a to 24c and the electronic parts provided in the apparatus body 2.

In the structure, three projections 24a to 24c are provided. Both the left and right projections 24a, 24c may be removed with the central projection 24b alone left as it is.

According to the above-embodiments, the following inconveniences do not occur. When the case is inclined so as to, for example, transport the case to some other place, and even though the disk is moved on such an occasion from the disk storage recess of the tray in the backward disk-disengaging direction, the disk neither gets over the projection, which is extended downward from the portion of the lower surface of the top plate of the case which is close to the rear portion of the tray, nor is disengaged from the recess in the backward direction. Therefore, a so-called avalanche phenomenon can be prevented reliably, and the disk can be stayed on the tray. As a result, the disk can be taken out smoothly to the outside of the case owing to the forward movement of the tray.

Since the projection is made of a synthetic resin, there is not the possibility that the electric short-circuiting occurs between the projection and electronic parts in the apparatus body.

Since the top plate and projection of the case are molded so as to be integral with each other, a projection-carrying top plate can be mass-produced inexpensively.

According to the above-embodiments, even through the disk is being disengaged from the interior of the disk storage recess of the tray in the backward direction when the case is inclined so as to, for example, transport the disk apparatus to some other place, the disk neither gets over the projections, which are extended downward from the portion of the lower surface of the top plate of the case which is close to the rear portion of the tray, nor is disengaged from the recess in the backward direction. Since the lower ends of the projections are positioned lower than the upper surface of the tray, the disk is not disengaged from the recess in the backward direction through a space under the projections. Therefore, a so-called avalanche phenomenon can be prevented reliably, and the disk can be stayed on the tray. The disk can be taken out smoothly to the outside of the case owing to the forward movement of the tray.

Since the projection is made of a synthetic resin, there is not the possibility that the electric short-circuiting occurs between the projections and electronic parts in the apparatus body.

According to the above-embodiments, the top plate and projections of the case are molded out of a synthetic resin so as to be integral with one another, so that the projection-carrying top plate can be mass-produced inexpensively.

The present invention is not limited to this but can be applied to various other types of disk apparatuses, for example, a DVD recorder for carrying out the reproduction, recording or erasing of information.

What is claimed is:

1. A disk apparatus in which a rectangular box type case is formed by a top plate, a bottom plate and a front plate, an apparatus body provided in the case having: a main chassis supporting a tray, on which a disk is placed, in such a manner that the tray can be moved forward and backward; and a driving chassis which is supported pivotably on the main chassis so that the driving chassis can be moved up and down, and which is mounted with an optical pickup and a turntable, a hook being projected from a circumferential portion of a disk storage recess of the tray, the disk being rotated at a high speed by the turntable, from a playing mode, in which the information recorded in the disk is read by the optical pickup, the driving chassis being moved up and down on the basis of an unloading signal, the disk being thereby handed over from the turntable to the tray, the tray being thereafter moved forward through a disk takeout port of the front plate, the disk being taken out from the tray with a new disk placed on the tray, a power source being turned off to stop the driving chassis in a downwardly moved state with the tray forcibly pushed in the rearward direction so that the tray is returned to the interior of the case the disengagement of the disk from the interior of the disk storage recess of the tray being prevented by the hook by inclining the case, characterized in that;

the hook is removed, projections being extended downward from the portion of a lower surface of the top plate which is close to a rear portion of the tray stored in the case, the projections being positioned at lower ends thereof lower than an upper surface of the tray, the case being made of a synthetic resin, the top plate of the case and projections being formed so as to be integral with each other.

2. A disk apparatus having a rectangular box type case formed by a top plate, a bottom plate and a front plate, an apparatus body provided in the case, the apparatus body having a main chassis supporting a tray, on which a disk is placed, in such a manner that the tray can be moved forward and backward, and a driving chassis which is supported pivotably on the main chassis so that the driving chassis can be moved up and down, and which is mounted with an optical pickup, the disk being rotated at a high speed by a turntable, from a playing mode in which the information recorded in the disk is read by the optical pickup, the driving chassis being moved up and down on the basis of an unloading signal, the disk being thereby handed over from the turntable to the tray, the tray being thereafter moved forward through a disk takeout port of the front plate, the disk being taken out from the tray with a new disk placed on the tray, a power source being turned off to stop the driving chassis in a downwardly moved state with the tray forcibly pushed in the rearward direction so that the tray is returned to the interior of the case, characterized in that projections of a synthetic resin are extended downward from the portions of a lower surface of the top plate which are close to a rear portion of the tray stored in the case, lower ends of the projections being positioned lower than an upper surface of the tray.

3. A disk apparatus according to claim 2, wherein the case is made of a synthetic resin, and wherein the top plate and projections of the case being molded are integrally formed one another.

* * * * *